US006045804A

United States Patent [19]
Persing

[11] Patent Number: 6,045,804
[45] Date of Patent: Apr. 4, 2000

[54] METHOD FOR DETECTING B. BURGDORFERI INFECTION

[75] Inventor: David H. Persing, Rochester, Minn.

[73] Assignee: Mayo Foundation for Medical Educational Research, Rochester, Minn.

[21] Appl. No.: 08/612,231

[22] Filed: Mar. 7, 1996

[51] Int. Cl.[7] .......................... A01N 63/00; A61K 39/00; A61K 39/02; C12Q 1/00
[52] U.S. Cl. ................... 424/234.1; 424/200; 424/184.1; 424/93.1; 424/93.4; 435/69.1; 435/69.3; 435/4; 435/7.2; 435/7.92
[58] Field of Search .............................. 424/200.1, 234.1, 424/93.1, 93.4, 184.1; 435/69.1, 69.3, 4, 7.2, 7.92

[56] References Cited

U.S. PATENT DOCUMENTS

| | | | |
|---|---|---|---|
| 5,279,938 | 1/1994 | Rosa | 435/6 |
| 5,530,103 | 6/1996 | Livey et al. | 530/416 |

FOREIGN PATENT DOCUMENTS

| | | | |
|---|---|---|---|
| 2001328 | 4/1924 | Canada | A61K 39/02 |
| 93/08306 | 4/1993 | WIPO . | |
| 9535119 | 12/1995 | WIPO | A61K 39/02 |

OTHER PUBLICATIONS

J. F. Anderson, et al., "Variants of the Prototype Borrelia burgdorferi B31 Strain Isolated from Ixodes scapularis", Proceedings of the VI International Conference on Lyme Borreliosis, pp. 23–26, (Jun. 19–22, 1994).
J. S. Bakken, el al., "Human Granulocytic Ehlichiosis in the Upper Midwest United States", JAMA, 272, 212–218, (Jul., 1994).
A. G. Barbour, "Isolation and Cultivation of Lyme Disease Spirochetes", Yale J. Biol. Med., 57, 521–525, (1984).
S. W. Barthold, "A Rat Model of Lyme Disease", Abstract of NIH Grant No. AI26815 (Funding year: 1994).
S. W. Barthold, et al., "Circumvention of Outer Surface Protein A Immunity by Host–Adapted Borrelia burgdoferi", Infect. Immun., Jun., 1995, 2255–2261, (Jun., 1995).
J. L. Benach, et al., "Spirochetes Isolated from the Blood of Two Patients with Lyme Disease", New England J. Med., 308, 740–742, (Mar., 1983).
S. Bergsrom, "Borrelia burgdorferi OspA and OspB Genes for Major Outer Membrane Proteins", GenBank, Accesssion No. X14407, (Aug. 27, 1993).
S. Bergstrom, "Molecular Analysis of Linear Plasmid—Encoded Major Surface Proteins, OspA and OspB, of the Lyme Disease Spirochete Borrelia burgdorferi", Mol. Micriobiol., 4, 479–486, (1989).
W. Burgdorfer, et al., "Erythema chronicum migrans—a Tickborne Spirochetosis", Acta Tropica, 40, 79–83, (1983).
G. D. Cimino, et al., "Post–PCR Sterilization: A Method to Control Carryover Contamination for the Polymerase Chain Reaction", Nucl. Acids Res., 19, 99–107, (1990).

J. S. Dumler, et al., "Ehrlichial Diseases of Humans: Emerging Tick–Borne Infections", Clinical Infectious Diseases, 20, 1102–1110, (1995).
J. J. Dunn, et al., "Outer Surface Protein A (OspA) form the Lyme Disease Spirochete, Borrelia burgdorferi: High Level Expression and Purification of a Soluble Recombinant From of OspA", Protein Expression and Purification, 1, 159–168, (1990).
H. Eiffert, "B. burgdorferi ospA Gene for OspA Outer Surface Protein", GenBank, Accession No. X60300 and S99475, (Dec. 7, 1992).
E. Fikrig, et al., "B. burgdorferi Outer Surface Protein A (ospA) Gene", GenBank, Accession No. M57248 and M38375, (Nov. 14, 1991).
E. Fikrig, et al., "Borrelia burgdorferi Strain 25015: Characterization of Outer Surface Protein A and Vaccination Against Infection", J. Immunol., 148, 2256–2260, (Apr., 1992).
E. Fikrig, et al., "Elimination of Borreliia burgdorferi from Vector Ticks Feeding on OspA–Immunized Mice", Proc. Natl. Acad. Sci., USA, 89, 5418–5421, (Jun., 1992).
E. Fikrig, et al., "Evasion of Protective Immunity by Borrelia burgdorferi by Truncation of Outer Surface Protein B", Proc. Natl. Acad. Sci, 90, 4092–4096, (1993).
E. Fikrig, et al., "Long–Term Protection of Mice from Lyme Disease by Vaccination with OspA", Infect. Immun., 60, 773–777, (Mar., 1992).
E. Fikrig, et al., "Outer Surface Protein A (Borrelia burgdorferi, Strain 35015,", GenBank, Accession No. S88693, (Jun. 10, 1992).
E. Fikrig, et al., "Protection of Mice Against the Lyme Disease Agent by Immunizing with Recombinant OspA", Science, 250, 553–556, (Oct., 1990).
E. Fikrig, et al., "Serologic Diagnosis of Lyme Disease Using Recombinant Outer Surface Proteins A and B and Flagellin", J. Infectious Diseases, 165, 1127–1132, (1992).
C. F. Garon, "Structural Characterization of Microbial Genes and Nucleic Acid Molecules", Abstract of NIH Grant No. AI00554 (Funding year: 1994).
M. A. Gerber, et al., "Recombinant Outer Surface Protein C Elisa for the Diagnosis of Early Lyme Disease", J. Infect. Dis., 171, 724–727, (Mar., 1995).
E. Godfroid, et al., "B. burgdorferi (G25) ospA Geen for Outer Surface Protein A", GenBank, Accession No. Z29086, (Dec. 20, 1993).

(List continued on next page.)

Primary Examiner—James C. Housel
Assistant Examiner—V. Ryan
Attorney, Agent, or Firm—Schwegman, Lundberg Woessner & Kluth, P. A.

[57] ABSTRACT

The present invention provides a method for detecting B. burgdorferi infection utilizing an antigen preparation lacking a detectable level of outer surface protein A (OspA). The antigen preparation is made from an isolate of B. burgdorferi that lacks the plasmid encoding outer surface protein A (OspA). The method of the invention discriminates B. burgdorferi infection from OspA vaccination.

11 Claims, 6 Drawing Sheets

OTHER PUBLICATIONS

E. Godfroid, et al., "B burgdorferi (VS461) ospA Gene for Outer Surface Protein A", *GenBank*, Accession No. Z29087, (Dec. 20, 1993).

J. L. Goodman, et al., "Molecular Detection of Persistant Borrelia burgdorferi in Urine of Patients with Active Lyme Disease", *Infect. Immun.*, 59, 269–278, (1991).

E. C. Guy, et al., "Detection of Borrelia burgdorferi in Patients with Lyme Disease by the Polymerase Chain Reaction", *J. Clin. Pathol.*, 44, 610–611, (1991).

M. Johsson, et al., "Hetergeneity of Outer Membrane Proteins in Borrelia burgdorferi: Comparison of osp Operons of Three Isolates of Different Geographic Origins", *Infection Imm.*, 60, 1845–1853, (1992).

D. Keller, et al., "Safety and Immunogenicity of a Recombinant Outer Surface Protein A Lyme Vaccine", *JAMA*, 271, 1764–1768, (1994).

C. P. Kolbert, et al., "Two Geographically Distinct Isolates of Borrelia burgdorferi from the United States Share a Common Unique Ancestor", *Res. Microbiol.*,146, 415–424, (1995).

D.U. Leong, et al., "PCR Detection of bacteria Found in Cerebrospinal Fluid", In: *Diagnostic Molecular Microbiology: Principles and Applications*, D. H. Persing et al., (eds.), American Society for Microbiology, Washington, D.C., 300–308, (1993).

M. R. Liebling, et al., "The Polymerase Chain Reaction for the Detection of Borrelia burgdorferi in Human Body Fluids", *Arthritis Rheum.*, 36, 665–675, (1993).

B. J. Luft, "B. burgdorferi ospA Gene for Outer Surface Protein A", *GenBank*, Accession No. X63387, (Jan. 12, 1994).

B. J. Luft, "B burgdorferi OspA Gene; Outer Surface Protein A", *GenBank*, Accession No. X62624, (Jan. 12, 1994).

L. A. Magnarelli, "Current Status of Laboratory Diagnosis for Lyme Disease (Review)", *Am. J. Medicine*, 98, 12S–14S, (1995).

S. E. Malawista, et al., "Failure of Multitarget Detection of Borrelia burgdorferi–Associated DNA Sequences in Synovial Fluids of Patients with Juvenile Rheumatoid Arthritis: A Cautionary Note", *Arthritis Rheum.*, 35, 246–247, (Feb., 1992).

S. E. Malawista, "Probes for Borrelia burgdorferi DNA in Ticks, Mice and Men", *Abstract of NIH Grant No. AI30548 (Funding Year: 1994)*.

D. C. Malloy, et al., "Detection of Borrelia burgdorferi Using the Polymerase Chain Reaction", *J. Clin. Microbiol.*, 28, 1089–1093, (1990).

Marconi, et al., "Variability of osp genese and gene products among species of Lyme disease spirochetes", *1993. Inf. Immun.* 61:2611–2617.

L. E. Mertz, et al., "Ticks, Spirochetes, and New Diagnostic Tests for Lyme Disease", *Mayo Clin. Proc.*, 60, 402–406, (1985).

P. D. Mitchell, et al., "Isolation of Borrelia burgdorferi From Skin Biopsy Specimens of Patients with Erythema migrans", *Am. J. Clin. Pathol.*, 99, 104–107, (Jan., 1993).

S. L. Nielsen, et al., "Detection of Borrelia burgdorferi DNA by the Polymerase Chain Reaction", *Mol. Cell. Probes*, 4, 73–79, (1990).

J. J. Nocton, et al., "Detection of Borrelia burgdorferi DNA by Polymerase Chain Reaction in Synovial Fluid from Patients with Lyme Arthritis", *N. Eng. J. Med.*, 330, 229–234, (1994).

D. H. Persing, et al., "Amplification Product Inactivation Methods", in *Diagnostic Molecular Microbiology: Principles and Applications*, D.H. Persing et al., Eds., American Society for Microbiology, Washington D.C., 105–121, (1993).

D. H. Persing, et al., "Detection of Babesia microti by Polymerase Chain Reaction", *J. Clin. Microbiol.*, 30, 2097–2103, (1992).

D. H. Persing, et al., "Detection of Borrelia burgdorferi Infection in Ixodes damnini Ticks with the Polymerase Chain Reaction", *J. Clin. Microbiol.*, 28, 566–572, (1990).

D. H. Persing, et al., "Detection of Borrelia burgdoferi DNA in Museum Specimens of Ixodes damnini Ticks", *Science*, 249, 1420–1423, (1990).

D. H. Persing, et al., "In Vitro Nucleic Acid Amplification Techniques", in *Diagnostic Molecular Microbiology: Principles and Applications*, D.H. Persing et al., Eds., American Society for Microbiology, Washington D.C., 51–87, (1993).

D. H. Persing, "Molecular Detection of Borrelia burgdorferi", in *Lyme Disease: Molecular and Immunologic Approaches*, S. Schuster, ed., Cold Spring Harbor Laboratory Press, Cold Spring Harbor, NY, 299–315, (1993).

D. H. Persing, "Molecular Diagnosis and Monitoring of Lyme Disease", Abstract of National Institutes of Health Grant No. AR41497, (Funding Year: 1994).

D. H. Persing, "Multi–Locus Molecular Detection of Borrelia Burgdorferi", Abstract of National Institutes of Health Grant No. AI32403, (Funding Year: 1994).

D. H. Persing, et al., "Multi–Target Detection of B. burgdorferi–Associated DNA Sequences in Synovial Fluids of Patients with Arthritis", *Arthritis Rheum.*, 33, Abstract No. 162, (suppl) s36, (1990).

D. H. Persing, et al., "Target Imbalance: Disparity of Borrelia burgdorferi Genetic Material in Synovial Fluid from Lyme Arthritis Patients", *J. Infect. Dis.*, 169, 668–672, (1994).

D. H. Persing, et al., "Target Selection and Optimization of Amplification Reactions", in *Diagnostic Molecular Microbiology: Principles and Applications*, D.H. Persing et al., Eds., American Society for Microbiology, Washington D.C., 88–104, (1993).

R. N. Picken, "Lyme Disease Diagnosis by PCR/DNA Probe System", Abstract of National Institutes of Health Grant No. AR41517, (Funding Year: 1994).

R. N. Picken, "Polymerase Chain Reaction Primers and Probes Derived from Flagellin Gene Sequences for Specific Detection of the Agents of Lyme Disease and North American Relapsing Fever", *J. Clin. Microbiol.*, 30, 99–114, (1992).

P. A. Rosa, et al., "A Specific and Sensitive Assay for the Lyme Disease Spirochete Borrelia burgdorferi Using the Polymerase Chain Reaction", *J. Infect. Dis.*, 160, 1018–1029, (1989).

P. N. Rys, "PCR Detection of Borrelia burgdorferi", in *Diagnostic Molecular Microbiology: Principles and Applications*, D.H. Persing, et al., Eds., American Society for Microbiology, Washington D.C., 203–210, (1993).

P. N. Rys, et al., "Preventing False Positives: Quantitative Evaluation of Three Protocols for Inactivation of Polymerase Chain Reaction Amplfication Products", *J. Clin. Microbiol.*, 31, 2356–2360, (1993).

T. G. Schwan, et al., "Induction of an Outer Surface Protein on Borrelia burgdorferi During Tick Feeding", *Proc. Natl. Acad. Sci., USA*, 92, 2909–2913, (Mar., 1995).

I. Schwartz, et al., "Diagnosis of Early Lyme Disease by Polymerase Chain Reaction Amplification and Culture of Skin Biopsies from Erythema Migrans Lesions", GenBank, Accession No. M88330 (Dec. 5, 1992).

I. Schwartz, et al., "Diagnosis of Early Lyme Disease by Polymerase Chain Reaction Amplification and Culture of Skin Biopsies from Erythema Migrans Lesions", *J. Clin. Micro.*, 30, 3082–3088, (1992).

I. S. Schwartz, "Nucleic Acid–Based Diagnostic Probes for Lyme Disease", Abstract of National Institutes of Health Grant No. AR41511, (Funding Year: 1994).

M. I. Sogin, "Amplification of Ribosomal RNA Genes for Molecular Evolution Studies", *In: PCR Protocols: A Guide to Methods and Applications*, Innis, et al., (eds.), Academic Press, San Diego, 307–314, (1990).

R. Sommer, et al., "Minimal Homology Requirements for PCR Primers", *Nuc. Acids Res.*, 17, 6749, (1989).

A. C. Steere, et al., "Erythema chronicum migrans and Lyme Arthritis: Epidemiologic Evidence for a Tick Vector", *Am. J. Epidemiol.*, 108, 312–321, (1978).

A. C. Steere, et al., "Erythema chronicum migrans and Lyme Arthritis", *Annals Int. Med.*, 86, 685–698, (1977).

A. C. Steere, et al., "Lyme Arthritis—An Epidemic of Oligoarticular Arthritis in Children and Adults in Three Connecticut Communities", *Arthritis and Rheum.*, 20, 7–17, (1977).

A. C. Steere, "Lyme Disease: A Growing Threat to Urban Populations", *Proc. Natl. Acad. Sci., USA*, 91, 2378–2383, (Mar., 1994).

A. C. Steere, "Lyme Disease", *N. Engl. J. Med.*, 321, 586–596, (1989).

A. C. Steere, et al., "The Spirochetal etiology of Lyme Disease", *New England J. Med.*, 308, 733–740, (Mar., 1983).

C. K. Stover, et al., "Protective Immunity Elicited by Recombinant Bacille Calmette–Guerin (BCG) Expressing Outer Surface Protein A (OspA) Lipoprotein: A Candidate Lyme Disease Vaccine", *J. Exp. Med.*, 178, 197–209, (1993).

F. C. Tenover, et al., "Nucleic Acid Probes for Detection and Identification of Infectious Agents", in Diagnostic Molecular Microbiology: Principles and Applications, D.H. Persing et al., Eds., American Society for Microbiology, Washington D.C., 3–25, (1993).

R. Wallich, "B. burgdorferi OspA Gene for Outer Surface Protein A", Genbank Accessing No. X66065 and S46718, (Jul. 25, 1993).

R. Wallich, "B. burgdorferi OspA Gene for Outer Surface Protein A", Genbank Accession No. X16467, (Jan. 2, 1990).

R. Wallich, "B. burgdorfi OspA Gene for Outer Surface Protein A", Genbank Accession No. X68059 and S46719, (Sep. 20, 1993).

R. Wallich, et al., "Evaluation of Genetic Divergence Among Borrelia burgdorferi Isolates by Use of OspA, fla, HSP60, and HSP70 Gene Probes", *Inf. Immun.*, 60, 4856–4966, (1992).

T. J. White, "Amplification Product Detection Methods", in Diagnostic Molecular Microbiology: Principles and Applications, D.H. Persing et al., Eds., American Society for Microbiology, Washington D.C., 138–148, (1993).

T. J. White, et al., "The Polymerase Chain Reaction: Clinical Applications", *Adv. Clin. Chem.*, 29, 161–196, (1992).

W. V. Williams, et al., "Detection of Borrelia burgdoferi by DNA Amplification", *Arthritis Rheum.*, 33, Abstract No. 161, (suppl) S36, (1990).

W. V. Williams, et al., "Molecular Diagnosis of Borrelia burgdorferi Infection (Lyme Disease)", *DNA Cell Biol.*, 11, 207–213, (1992).

G. Zumstein, et al., "Genetic Polymorphism of the Gene Encoding the Outer Surface Protein A (OspA) of Borelia burgdorferi", *Med. Microbiol. Immunol.*, 181, 57–70, (1992).

G. Zumstein, et al., "OspA=Outer Surface Protein A [Borrelia burgdorferi, skin isolate PKo, Genomic, 882 nt]", Genbank Accession No. S48322, (Jan. 8, 1993).

G. Zumstein, et al., "OspA=Outer Surface Protein A [Borrelia burgdorferi, cerebrospinal fluid isolate PBi, Genomic, 839 nt]", Genbank Accession No. S48323, (Jan. 14, 1993).

Anderson et al. Journal of Clinical Microbiology 34(3): 524–529, 1996 (Mar.).

Sadziene et al. Infection and Immunity 61(5): 2192–2195, 1993.

Coonrod. "Immunologic Diagnosis". In: Infectious Diseases 5$^{th}$ ed. PD Hoeprich et al (eds). JB Lippincott Co., Philadelphia, 1994 pp. 187–194.

Barbour, "Lyme Disease". In: Infectious Diseases 5$^{th}$ ed. PD. Hoeprich et al. (eds). J.B Lippincott Co., Philadelphia, 1994. pp. 1327–1332.

Anderson et al. Proceedings of the VI International Cong. on Lyme Borreliosis. Bologna, Italy Jun. 19–22, 1994. Cevenini et al (eds). pp. 23–26.

Norton–Hughes et al. Infection and Immunity 61(12): 5115–5122, 1993.

Sadziene et al. Journal of Exp. Med 176: 799–809, 1992.

Anderson et al. Journal of Clinical Microbiology 34(3): 524–529, 1996 (Feb.).

New Riverside University Dictionary. 1994. p. 630.

METHOD FOR DETECTING B. BURGDORFERI INFECTION

The present invention was made with the support of the U.S. Government under Center for Disease Control cooperative agreement U50/CCU-510343, and Public Health Service grants A1-32403, BAA-9431, AR-40452, A1-30548 and A1-41497. The U.S. Government has certain rights in the invention.

INTRODUCTION

Lyme disease is a tick-transmitted disorder involving multiple organ systems. The causative agent has been identified as the spirochete *Borrelia burgdorferi*. Lyme disease is one of the most common tick-transmitted diseases worldwide and the most common such zoonosis in the United States. From 1986 to 1991, over 40,000 cases of disease were reported to the Centers for Disease Control. Most cases are clustered in highly endemic areas of the northeast and Great Lakes regions of the U.S., but cases have now been reported in 47 states. Although many of these states are not considered endemic areas, widespread public concern about exposure to the disease, coupled with its largely nonspecific clinical presentation, has placed tremendous demands for high sensitivity and specificity in the serodiagnosis of *B. burgdorferi* infection.

Public concern about Lyme disease has also provided motivation for the development of vaccines. Recombinant vaccines based on purified preparations of outer surface protein A (OspA) from *B. burgdorferi* sensu stricto have been shown to be effective in preventing transmission of *B. burgdorferi* in experimental animal models (E. Fikrig et al., *Infect. Immun.*, 60, 773–7 (1992); E. Fikrig et al., *Science*, 250, 553–6 (1990)), and are now being tested in humans. The advent of successful recombinant vaccines for prevention of Lyme disease is an important application of basic research on *B. burgdorferi*. Such vaccines, if shown to be safe and effective, will likely be administered widely in Lyme disease endemic areas of the upper Midwestern and northeastern United States, thus reducing the morbidity and occasional mortality associated with the disease. Ironically, however, the availability of such vaccines may increase the level of diagnostic uncertainty in the evaluation of patients with presentation of a nonspecific flu-like illness after tick bite or so-called "summer flu," the majority of which may be due to unrelated causes, to diseases transmitted by ticks such as *B. microti*, or to granulocytic Ehrlichia spp. Additional uncertainty may arise if the vaccines are not completely protective; vaccinated patients with multisystem complaints characteristic of later presentations of Lyme disease may be difficult to distinguish from patients with vaccine failure. Vaccine failures have been occasionally noted in animal models (E. Fikrig et al., *Science*, 250, 553–6 (1990)), and infection with antigenically variant strains of *B. burgdorferi*, which are being increasingly documented in the U.S., might still occur.

In theory, Western blot analysis could be used to discriminate the vaccinated state from true infection. Electrophoretically separated *B. burgdorferi* proteins would be used to probe subject serum to detect the presence of *B. burgdorferi* antibodies in the serum. However, Western blot analysis is impractical as a screening method; it is subject to variations in antigen composition and concentration, input serum amounts, and blot interpretation. In part because of these uncertainties, no Lyme disease Western blot assays have received FDA clearance to date. Moreover, if the number of vaccinated subjects in endemic areas becomes large, the increased cost of Western blot evaluation after "false positive" screening immunoassays may become prohibitively high.

Currently, the most widely used screening test for Lyme disease is an enzyme-linked immunosorbent assay (ELISA) based on a whole cell antigen preparation from *B. burgdorferi* strain B31. However, anti-OspA antibodies present in serum of vaccinated subjects may react with OspA present in the antigen preparation, resulting in serologic false positivity. There is, therefore, a demonstrated need for a cost effective and easily employed diagnostic test for Lyme disease that can not only detect infection by *B. burgdorferi* but which can discriminate between subjects harboring a true *B. burgdorferi* infection and subjects who have been vaccinated with OspA.

SUMMARY OF THE INVENTION

The present invention provides an antigen preparation and a method of using the antigen preparation to detect mammalian infection by the spirochete *B. burgdorferi*. A solid substrate comprising the antigen preparation of the invention immobilized thereon is also provided. The antigen preparation of the invention differs from other *B. burgdorferi* preparations used to detect anti-*B. burgdorferi* antibodies produced in response to *B. burgdorferi* infection in that the antigen preparation of the invention lacks a detectable level of outer surface protein A (OspA). The antigen preparation of the invention is derived from a cell lysate of a *B. burgdorferi* isolate, which isolate lacks a detectable level of OspA.

The gene for OspA is known to be present on a ca. 48–55 kB linear plasmid in *B. burgdorferi*. Thus, the antigen preparation of the invention is preferably made from a cell lysate of a *B. burgdorferi* isolate lacking the plasmid containing the gene encoding OspA. Isolates preferred for use in making the antigen preparation include *B. burgdorferi* isolates 49736, 46047, 48510, 46794, and 50772. Pursuant to the Budapest Treaty, representative samples of *B. burgdorferi* isolates 49736, 48510, 46047, 50772, and 46794 were deposited in the American Type Culture Collection (ATCC), 10801 University Boulevard, Manassas, Va., U.S.A., under accession numbers 69973, 202204, 202205, 202207, and 202208, respectively. *B. burgdorferi* isolate 49736 was deposited on Jan. 11, 1996, and isolates 48510, 46047, 50772, and 46794 were deposited on Mar. 11, 1999. Viability of isolate 49736 was tested on Jan. 19, 1996 and the viability of isolates 48510, 46047, 50772, and 46794 was tested on Mar. 18, 1999. These deposits were made by Dane Mathiesen on behalf of Mayo Clinic and David H. Persing, 501 Guggenheim, 200 First Street S.W., Rochester, Minn. 55905. These deposits are capable of reproduction. A particularly preferred antigen preparation is derived from a cell lysate of *B. burgdorferi* isolate 49736.

The steps of the diagnostic method provided by the invention include:

(a) contacting the antigen preparation of the invention immobilized on a solid substrate with a sample of physiological fluid suspected of containing antibodies to *B. burgdorferi* for a time sufficient to allow formation of a binary complex between the immobilized antigen preparation and at least a portion of the antibodies; and (b) detecting the presence of the binary complex on the solid substrate.

The presence of a binary complex is indicative of a *B. burgdorferi* infection.

The invention also provides a diagnostic kit for detecting a *B. burgdorferi* infection, which includes packaging containing, separately packaged, the antigen preparation of the invention, preferably immobilized on a solid substrate, and an anti-human immunoglobulin having a detectable label or a binding site for a detectable label.

DETAILED DESCRIPTION OF THE INVENTION

Figure 1:
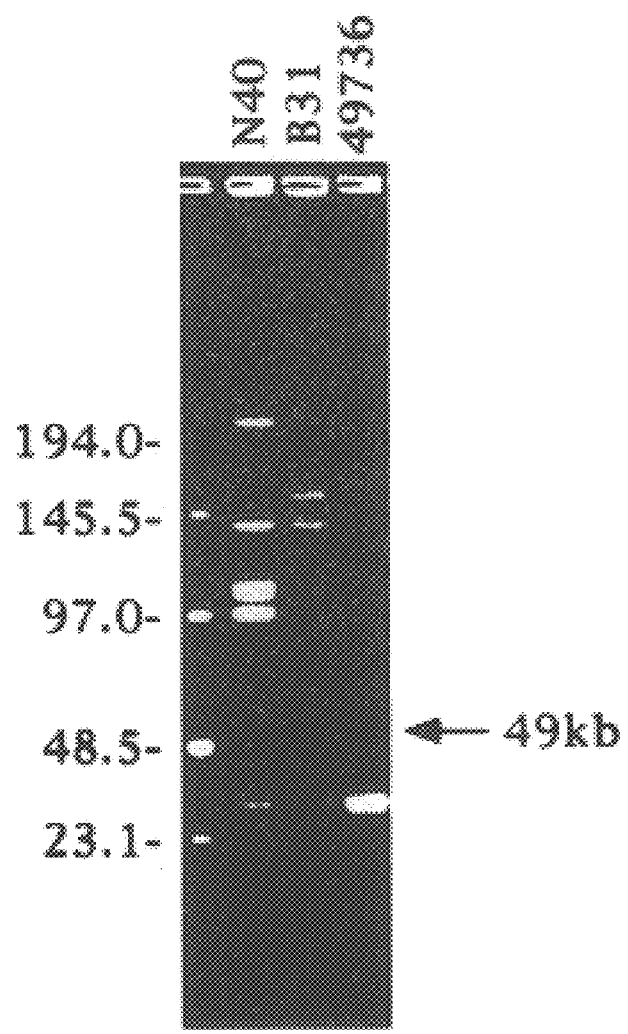
FIG. 1. Pulsed field gel electrophoretic (PFGE) analysis of mluI-digested genomic and plasmid DNA from *B. burgdorferi* isolates B31, N40 and 49736.

Lyme disease vaccines can be prepared utilizing outer surface protein A (OspA) from *B. burgdorferi* (E. Fikrig et al., *Science,* 250:553–6 (1990)). Physiological fluids from a vaccinated subject, such as a human or a domestic animal, can therefore be expected to contain antibodies to OspA. The presence of anti-OspA antibodies in subject serum makes it difficult to detect or confirm an infection by the spirochete *B. burgdorferi* in vaccinated individuals, because current diagnostic methods are based on a reaction between antibodies in subject serum and an antigen preparation made from a *B. burgdorferi* cell lysate that contains OspA, which can result in serologic false positive responses.

The present invention provides an antigenic *B. burgdorferi* preparation lacking a detectable level of OspA. False positive reactions in OspA-vaccinated subjects are eliminated when this antigen preparation is utilized to detect *B. burgdorferi* infection in such individuals, since the preparation does not react with the anti-OspA antibodies present in the sera due to vaccination.

The antigen preparation provided by the invention is derived from a cell lysate of an isolate of *B. burgdorferi,* which isolate lacks a detectable level of outer surface protein A (OspA). That is, the level of OspA in the antigen preparation, if any, is insufficient to cause a positive result using techniques known in the art to detect the formation of a bivalent complex between OspA and anti-OspA antibodies. The antigen preparation is "derived from" a cell lysate of a suitable isolate in that a cell lysate of the isolate is used as a starting material for the making of the antigen preparation. Cells may be lysed by any convenient method, such as sonication or French press. Preferably, the cell lysate from which the antigen preparation is derived has less than 3% of the molar concentration of OspA present in a comparable cell lysate of wild-type *B. burgdorferi* strain B31 or N40. A "comparable" cell lysate is a cell lysate prepared using procedures (e.g. lysing method, nature and volume of reagents and buffers, experimental conditions such as temperature and pressure, and the like) equivalent to those used to prepare a cell lysate from which the antigen preparation of the invention is derived. More preferably, the cell lysate from which the antigen preparation is derived has less than 1% of the wild-type molar concentration of OspA in a comparable cell lysate of *B. burgdorferi* strain B31 or N40.

The antigen preparation is preferably derived from a *B. burgdorferi* isolate that lacks the ca. 48–55 kB plasmid known to contain the gene encoding OspA. Copies of the gene for OspA are presently not known to be encoded by any genomic or plasmid DNA in *B. burgdorferi* other than the ca. 48–55 kB linear plasmid; however, any isolate or strain possessing, either on a plasmid or in its genome, a number of copies of the OspA gene sufficient to produce a detectable level of OspA would be unsuitable for use in the invention.

The plasmid known to contain the gene that encodes OspA is about 48–55 kB in size. Typically, it is about 53 kB. The plasmid also contains the gene that encodes OspB. Thus, an antigen preparation made from a cell lysate of a *B. burgdorferi* isolate lacking the 53 kB plasmid will also lack detectable levels of OspB and, consequently, can be utilized in a method that discriminates between *B. burgdorferi* infection and vaccination with OspB.

The present invention utilizes certain isolates of *B. burgdorferi* which do not contain OspA plasmid. However, it is believed that other isolates of *B. burgdorferi* lacking detectable levels of OspA may exist that can be identified using techniques well known to one of skill in the art of molecular biology. For example, the presence of OspA (a 31 kD protein) can be detected electrophoretically by subjecting a cell lysate and a set of molecular weight markers to SDS-PAGE, then inspecting the gel for a band corresponding to a protein having a molecular weight of approximately 31 kD. Presence or absence of OspA can be subsequently confirmed by subjecting the gel to Western blot analysis, whereby the gel is contacted with anti-OspA antibodies and a suitable labeling technique is used to detect a binding reaction between the antibodies and a protein imbedded in the gel. A negative result indicates the absence of OspA, and the isolate would be suitable for use in the invention. Other methods of detecting the presence or absence of OspA include direct immunofluorescence, immunoelectron microscopy, two-dimensional gel electrophoresis, density gradient fractionation, and various chromatographic techniques, including high performance liquid chromatography.

Suitable isolates can also be identified by evaluating whether the candidate isolate possesses a gene encoding OspA. For example, presence or absence of a gene encoding OspA can be determined directly by polymerase chain reaction (PCR) utilizing primers designed to amplify regions of the OspA gene. Alternatively, cellular DNA can be subjected to pulsed field gel electrophoresis (PFGE), and presence or absence of the gene encoding OspA can be determined via Southern hybridization using a probe based on the known OspA nucleotide sequence.

Presence or absence of the 53 kB linear plasmid known to encode OspA can be determined using techniques well known to those skilled in the art of molecular biology, such as subjecting cellular OspA to pulsed field gel electrophoresis (PFGE) and comparing the resulting migration pattern to one produced by an isolate known to contain the plasmid. Other techniques useful in determining the presence or absence of the 53 kB plasmid containing the gene encoding OspA include conventional Southern hybridization techniques, dot blotting, PCR and electron microscopy.

Preferred isolates for use in making the antigen preparation of the invention include *B. burgdorferi* isolates 49736, 46047, 48510, 46794, and 50772, which have been found to lack the 53 kB plasmid encoding OspA. Particularly preferred is isolate 49736. An "isolate" differs from a "strain" in that an isolate may, but need not, contain a heterogeneous mixture of species or quasispecies, whereas a strain is a homogenous bacterial population typically obtained using successive cultures of single bacterial colonies. The spirochetes contained in a suitable *B. burgdorferi* isolate are very closely related genetically to one another and share the common feature of lacking the 53 kB plasmid found in wild-type strains. Any *B. burgdorferi* isolate or strain lacking the 53 kB plasmid encoding OspA and hence lacking a detectable level of OspA is suitable for use in the invention.

Isolates lacking detectable levels of OspA that are genetically related to *B. burgdorferi* strains N40 or B31, the strains known to cause most North American cases of Lyme disease, are especially suited for use in the invention. Isolates that are "genetically related" to strains N40 or B31 are those that are members of the B31 phylogenetic division and include *B. burgdorferi* isoates 49736, 46047, 48510, 46794 and 50772. These isolates are characterized by indistinguishable 23S rDNA sequences in a DNA segment spanning nucleotides 235 through 532 in the rDNA sequence (B31 numbering, GenBank Acc. No. M88330, B31 *B. burgdorferi*, 23S ribosomal DNA). Genetic relatedness to known infectious strains of *B. burgdorferi* is useful because it ensures that the antigen preparation will contain antigens that react with the antibodies produced in response to infection by those strains, yielding serologic true positive results.

The invention also provides a solid substrate having attached to or otherwise immobilized on the surface thereof the antigen preparation of the invention. The antigen preparation can be immobilized on the substrate in any convenient manner, such as via acid/base interactions, hydrophobic interactions, or glutaraldehyde cross-linking. Suitable solids include particulate substrates such as polystyrene beads, the wells of microtiter plates, paper, or synthetic fiber test strips, and the like. The solid surface having the antigen preparation attached thereto is useful to detect the presence of anti-OspA antibodies in a fluid with which it comes into contact, as disclosed more fully in the examples below.

The present invention provides a method useful to detect a *B. burgdorferi* infection in a subject. The method provided by the invention is particularly useful to discriminate *B. burgdorferi* infection from OspA vaccination, although it is sufficiently sensitive and specific to use in any general Lyme disease screening or diagnostic application. Thus, the method of the invention is particularly appropriate for large scale screening or diagnostic applications where only part of the subject population has been vaccinated or where the vaccination status of the population is unknown.

The method utilizes the antigen preparation of the invention to produce a detectable antibody-antigen complex. Specifically, the method provided by the invention for detecting *B. burgdorferi* infection utilizes the following steps:

(a) contacting the immobilized antigen preparation of the invention with a sample of physiological fluid suspected of containing antibodies to *B. burgdorferi* for a period of time sufficient to allow formation of a binary complex between the antigen preparation and at least a portion of the antibodies; and (b) detecting the presence of the binary complex on the solid substrate, wherein the presence of the binary complex is indicative of a *B. burgdorferi* infection.

The physiological fluid is preferably obtained from a human subject, although the method can utilize fluid obtained from veterinary sources. More preferably, the fluid is blood, blood serum, blood plasma, or cerebrospinal fluid. Most preferably, it is blood serum.

In a particularly preferred embodiment of the invention, physiological fluid is obtained from a subject, preferably a human subject, who has been inoculated with a vaccine made from all or a portion of outer surface protein A (OspA). "A portion" of OspA means a fragment of OspA effective to produce a detectable anti-OspA antibody response in a subject. The OspA fragment can be natural or recombinant, and may be chemically or enzymatically modified. It can be part of an antigenic recombinant fusion protein or chimeric protein made by joinder with all or a part of a second protein, such as glutathione transferase. Typically, the vaccine used to inoculate humans is made from a portion of OspA that includes the second half of the protein (i.e., the C-terminal half).

Where the antigen preparation used in the method is made from a *B. burgdorferi* isolate lacking the 53 kB plasmid known to encode OspA and OspB, the antigen preparation can be expected to lack detectable levels of both OspA and OspB. In this case, the method discriminates between *B. burgdorferi* infection and OspB vaccination where the fluid sample is obtained from a subject that has been inoculated with all or a portion of outer surface protein B (OspB).

The immobilized antigen is contacted with the sample to be assayed, e.g., with a physiological fluid such as blood serum, to form an antigen-antibody complex. The resultant bivalent complex of antigen and antibody is then detected, e.g., in the case of a sample of human physiological fluid, by reacting it with an anti-human IgG antibody which comprises a detectable label or a binding site for a detectable label. In the latter case, the binding site is reacted with a compound specific for the binding site, which compound comprises a detectable label. Useful detectable labels include enzymes, radiolabels, or fluorescent labels. The relative or absolute amounts of the resultant bivalent complex may be determined or quantified using spectrophotometry, radiometry, fluorescent or calorimetric techniques, or the like.

Conveniently, the method can be practiced as an enzyme-linked immunosorbent assay (ELISA) wherein the detectable label is typically alkaline phosphatase or horseradish peroxidase. Useful binding sites for detectable labels include avidin, biotin, and derivatives thereof, as well as natural antigenic sites that are bound by labelled antibodies. The resultant ternary or quaternary complex is then detected and/or quantified via the detectable label, i.e., via an enzyme-substrate color-forming reaction, radioemission, agglutination, or the like.

The antigen preparation of the invention is conveniently packaged in kit form, wherein two or more immunoreagents are separately packaged in predetermined amounts, within the outer packaging of the kit, which may be a box, envelope, or the like. The packaging also preferably comprises instruction means, such as a printed insert, a label, a tag, an audio or video cassette tape, and the like, instructing the user in the practice of the assay format.

A preferred embodiment of a diagnostic kit for evaluating *B. burgdorferi* infection comprises packaging containing, separately packaged: (a) the antigen preparation of the invention; and (b) anti-human immunoglobulin containing a detectable label or a binding site for a detectable label. More preferably, the antigen preparation is immobilized on a solid surface, such as a fibrous test strip, a well in a multi-well plastic microtiter plate, a test tube, or beads.

The invention will be further described by reference to the following detailed examples.

EXAMPLE I

Identification of a B. burgdorferi Isolate Lacking OspA

B. burgdorferi isolate 49736 was originally recovered from an Ixodes scapularis tick (also called Ixodes dammini) from New Jersey. This isolate and five others (46047, 48510, 46794, 48081 and 50772) were initially characterized as having unusual protein electrophoretic profiles by protein gel electrophoresis in that they lacked OspA and OspB bands. (J. F. Anderson et al., *Proc. VI Int'l Conf. on Lyme Borreliosis,* 23–26 (1994)).

A. Detection of the presence or absence of the ca. 53 kB plasmid containing the OspA Gene Genomic macrorestriction analysis of *B. burgdorferi* isolate 49736 by pulsed field gel electrophoresis (PFGE) was used to test for the presence or absence of the ca. 53 kB plasmid known to contain the gene encoding OspA. The results are shown in FIG. 1. *B. burgdorferi* strains N40, B31 (ATCC No. 35210), and 49736 (ATCC No. 69973) were grown to confluency in 10–20 ml BSK II media (Sigma Chemical Company, St. Louis, Mo.) containing 6% rabbit serum (Sigma Chemical Company, St. Louis, Mo.) and were harvested by centrifugation at 9,000×g for 15 minutes. The cell pellet was resuspended in 200 to 500 μl EET (100 mM EDTA, 10 mM EGTA, 10 mM Tris, pH 8.0) (Sigma Chemical Company, St. Louis, Mo.) and warmed to 42° C., then embedded carefully to an equal volume of 60° C. 1.6% SeaPlaque agarose (FMC BioProducts, Rockland, Me.) in EET. The final concentration of agarose was 0.8%. The plugs (50 μl) were digested overnight with mluI (3 μl at 10–12 U/μl) at 37° C., and the restriction fragments were separated in a 1.2% agarose (FMC) gel in a Bio-Rad Chef DR2 electrophoresis chamber containing pre-cooled (11–14° C.) 0.5×TAE (1×: 40 mM Tris-acetate, 20 mM acetic acid, 1 mM EDTA) and pre-run (no voltage) for 1 hour, then initial switch time of 1–5 second, a linear ramp with a final switch time of 10–20 seconds, and 200 V (6 V/cm) for 15–17 hours. Lane M in FIG. 1 contains a mixture of Lambda DNA Hind III fragments, Lambda DNA and Lambda concatemers (Sigma Chemical Company, St. Louis, Mo.) used as a molecular weight marker. The pulsed field gel was stained with ethidium bromide (Sigma Chemical Company, St. Louis, Mo.) and the DNA visualized with UV irradiation. After photography, the DNA was transferred from the pulsed field gel to a 0.2 μm supported nylon transfer and immobilization membrane (S&S Inc., Keene, N.H.). A probe specific for OspA (OspA6s-3a) was made by polymerase chain reaction (PCR) using OspA6s (5'-ATTGGGAATAGGTCTTAATATTAGCCT-3') as sense primer, OspA3a (5'-GCCATTTGAGTCGTATTGTTGTACTG-3') as antisense primer, and N40 genomic and plasmid DNA as the target. The membrane was probed to confirm the presence or absence of a gene encoding OspA. The probe labeling, hybridization and detection followed the protocols provided with the ECL Southern blotting system kit (Amersham International, England).

As shown in FIG. 1, isolate 49736 is related to *B. burgdorferi* strain N40, relatives of which are widely distributed in the northeastern United States, the Upper Midwest and California. These isolates are also closely related to strain B31, in contrast to isolates from moderate climates of the southeastern and southwestern United States, which are often related to strain 25015. However, in contrast to strain N40, isolate 49736 apparently lacked the ca. 53 kB plasmid species presumed to encode OspA and *B. This observation was verified by hybridizing Southern blots of the mluI digest with the OspA*6s-3a probe. In contrast to strains N40 and B31, which were strongly OspA probe positive, no detectable signal was observed in the digest derived from isolate 49736. This observation was consistent with the absence of the 53 kB plasmid species. Similar results were obtained from N40-like isolates 46047 and 48510, and B31-like isolates 46794 and 50772, which also lack the plasmid.

B. Direct Detection of the OspA Gene and Evaluation of 23S Ribosomal RNA Sequences The 23S ribosomal RNA and OspA gene segments of numerous *B. burgdorferi* isolates, including isolates 49736, 46047, 48510, 46794, and 50772 were amplified and sequenced to test for genetic relatedness and for the presence or absence of the gene encoding OspA. Oligonucleotide primers Bor23S A, Bor23S B, OspA 149S, and OspA 459A were synthesized in an oligonucleotide synthesizer (Applied Biosystems, Foster City, Calif.) and desalted on a sephadex G-25 column (Pharmacia Biotech, Piscataway, N.J.). Target DNA of each isolate was obtained through centrifugation (16,000×g) of 1–2 ml confluent culture in BSK media. The resulting cell pellets were resuspended in 50–100 μl TE (Tris-EDTA) or $H_2O$ and boiled for 15 minutes. The lysed whole cell mixture kept at −20° C. until use.

Portions of the 23S rRNA gene (region 181–590, B31 numbering) and the OspA gene (region 149–459, B31 numbering) of the selected Borrelia isolates were amplified by PCR. The 23S rRNA gene amplification was performed in a 100 μl reaction volume and contained 100 pmol of each primer (Bor23S A, 5'-GGGAAGTGAACCATCTAAGTACCCTGAG-3' and Bor23S B, 5'-ACGGTTTCAGTTCTATTTCACTCC-3'), 1× PCR buffer (Perkin Elmer Corp., Foster City, Calif.), 200 μM each of dNTPs, 1.5 mM $MgCl_2$, 10% glycerol, 2.5 units Taq DNA polymerase, and 5 μl of the lysed whole cell mixture. Reaction components were initially denatured at 94° C. for 4 minutes; subsequently, components were denatured at 94° C. for 45 seconds, annealed at 55° C. for 45 seconds and extended at 72° C. for 45 seconds, for a total of 30 cycles. Finally, tubes were incubated at 72° C. for 5 minutes to complete the extension. Of this 409 bp amplification product, the portion corresponding to 23S rDNA nucleotide positions 235–532 (B31 numbering) was sequenced as described below.

A 330 bp portion of the OspA gene was amplified in a 50 μl volume and contained 50 pmol of each primer (OspA 149S, 5'-TTATGAAAAAATATTTATTGGGAAT-3', OspA 459A, 5'-AGAAGATGGCAAAACACTAGT-3'), 1× PCR buffer, 200 μM each of dNTPs, 1.5 mM $MgCl_2$, 10% glycerol, 0.01% Tween 20, 2.5 units Taq DNA polymerase, and 2 μl of the whole cell mixture. With 40 cycles of denaturation at 94° C. for 1 minute, extension at 72° C. for 2 minutes, and early denaturation and final extension as above, the amplification was complete. The products were analyzed by electrophoresis in an agarose gel (1% SeaKem GTG-OspA PCR product, 3.5% Nusieve GTG/0.5% SeaKem GTG-23S rRNA PCR product, FMC), and visualized with 0.1% ethidium bromide staining and UV irradiation.

Amplification products from a minimum of three separate reactions per isolate were pooled and purified to minimize effects of random incorporation errors by Taq polymerase, then sequenced on an automated system (373A DNA sequencer, Applied Biosystems). Both sense and antisense strands were sequenced using the PCR amplification primers.

All isolates tested yielded the expected OspA amplification product except the *B. hermsii* controls (which lack the linear plasmid encoding OspA) and strains 49736, 46047, 48510, 46794, and 50772. Consistent with the PFGE results, sequencing of the portion of the 23S rDNA corresponding to nucleotide positions 235–532 (B31 numbering) showed these isolates to have 23S rDNA sequences indistinguishable from other members of the B31 phylogenetic division.

C. Detection of Outer Surface Protein A (OspA)

Polyacrylamide gel electrophoresis (PAGE) was used to test isolate 49736 for the presence or absence of outer surface protein A (OspA). *B. burgdorferi* N40 and 49736 were grown individually in BSK II medium containing 6% rabbit serum at 32° C. until confluent (ca. $1 \times 10^9$ cells/ml). The cell pellet from 1 ml culture was collected by microcentrifugation at 10,000×g for 5 min, then washed three times with phosphate buffered saline (PBS). The washed pellet was then lysed by adding 100 μl of 2× sodium dodecyl sulfate (SDS) gel-loading buffer with 100 mM dithiothreitol (Sigma Chemical Company, St. Louis, Mo.) and heating for 5 minutes at 95° C. Equal amounts of lysed cells from washed cell pellets (ca. $1 \times 10^8$ cells from confluent culture) were loaded into each lane. The 2.5 to 10 μl of cell lysate was separated by a 12% SDS-polyacrylamide gel. A low molecular weight marker (Sigma Chemical Company, St. Louis, Mo.) was used to determine the apparent molecular weights. The gel was then stained with Coomassie Brilliant Blue R250. After destaining, the gel was scanned with the ScanMaker (Microtek International Inc., Taiwan).

For immunoblotting, proteins were electrotransferred from SDS-polyacrylamide gel to a polyvinyldifluoride (PVDF) membrane (Millipore Corporation, Bedford, Mass.). The membrane was then blocked with 5% dry milk and 1% bovine serum albumin (BSA) overnight at 4° C., and incubated in monoclonal OspA antibody L1A151 (Monoclonal Core Facility, Mayo Clinics, Rochester, Minn.) with 1:3000 dilution for 2 hours. After washing with TBS (Tris-buffered saline) –0.1% Tween-20 3 times for 5 minutes each at room temperature, the membrane was incubated in horseradish peroxidase (HRP)-labeled anti-mouse second antibody (Amersham International plc, England) with 1:4,000 dilution for 1 hour. The membrane was subsequently washed 3 times with TBS-0.3% Tween-20 and 3 times more with TBS-0.1% Tween-20, 5 minutes for each washing. The signals were developed by incubating the membrane in ECL Western blotting detection reagents (Amersham International plc, England) for 1 minute. The film was exposed to the plastic wrapped membrane from 1 second to 1 hour.

Figure 2:
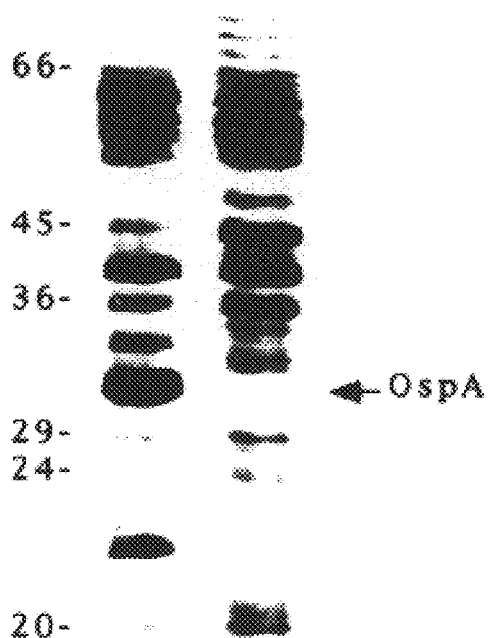
FIG. 2. Sodium dodecyl sulfate-polyacrylamide electrophoretic analysis of protein pattern for *B. burgdorferi* isolates N40 and 49736.
Figure 3:
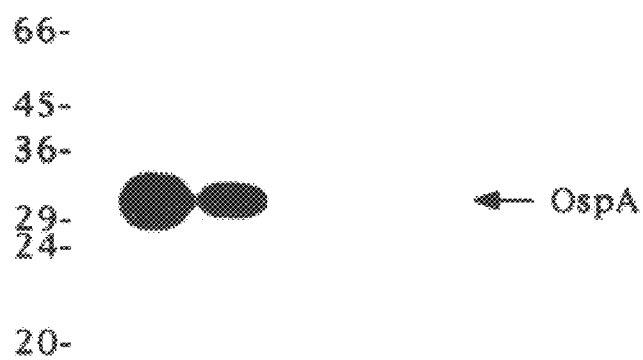
FIG. 3. Western blot analysis of OspA for *B. burgdorferi* isolates N40 and 49736.

The SDS-PAGE results, shown in FIG. 2, confirmed that, consistent with the absence of a gene encoding OspA, the characteristic 31 kD protein species encoded by that gene was absent in isolate 49736. Results from the Western blot analysis using a monoclonal antibody directed against OspA are shown in FIG. 3. Lane 1 contains N40 whole cell lysate (ca. $2.5 \times 10^7$ cells/lane); lane 2, prepared N40 ELISA antigen (0.5 μg total protein/lane) lane 3, prepared 49736ELISA antigen (1.4 μg total protein/lane); lane 4, 49736 whole cell lysate (ca. $1 \times 10^8$ cells/lane). Strains B31 and N40 contain a strongly reactive 31 kD species, but in isolate 49736, this species is absent. The latter strain harbors a ca. 21 kD protein species that migrates in the position expected for OspC; this is consistent with the finding that this strain comprises OspC by Western blot analysis.

EXAMPLE II

Enzyme-Linked Immunosorbent Assay (ELISA) Based on the OspA-Minus Variant for Detection of *B. burgdorferi* Infection A. Mouse Sera Four-week-old female C3H/HeJ mice were obtained from The Jackson Laboratory (Bar Harbor, Me.). The animals were shipped and housed in micro-isolator cages. Water was provided daily, and the animals were euthanized with carbon dioxide. The mice were infected with *B. burgdorferi* (strain N40) by syringe inoculation.

The *B. burgdorferi* isolate N40 used in these studies was grown to log phase in modified Barbour-Stoenner-Kelly (BSK) II medium (Sigma, St. Louis, Mo.) and counted using a hemocytometer under microscopy. Mice were killed between 14 and 21 days after inoculation. The blood was collected for ELISA testing before sacrifice, and tissues were collected for BSK culture to confirm the presence or absence of infection after sacrifice of the animals. Joints and hearts from all mice were histopathologically examined for disease.

B. Human Sera and Vaccination Studies

Six serum specimens from normal healthy donors were provided by the Mayo blood bank for use as negative ELISA controls. Twenty *B. burgdorferi* seroreactive specimens were obtained from patients from the Upper Midwest who had previously been analyzed by an immunoassay for detection of anti-*B. burgdorferi* antibody (L. E. Mertz et al., *Mayo Clinic Proceedings*, 60, 402–406 (1985)). Serum was obtained from an additional 21 patients who were enrolled in a recombinant OspA vaccine pilot study at the Yale Lyme disease clinic; all the Yale patients had previous histories of Lyme disease and most were still seropositive at the time of enrollment.

C. Enzyme-Linked Immunosorbent Assay (ELISA)

*B. burgdorferi* strains N40 and 49736 were grown individually in BSK II medium containing 6% rabbit serum at 32° C. until confluent (ca. $1 \times 10^9$ cells/ml). The cell pellets were harvested from 200 ml cultures by centrifugation at 20,000×g for 30 minutes at 4° C. The pellet was resuspended in PBS-Mg-Az (phosphate buffered saline 0.01 M, pH 7.2, $MgCl_2$ 5 mM, sodium azide 0.02%) and precipitated by centrifugation. This process was repeated three times. The washed pellet was resuspended in 40 ml of 1M NaCl in PBS-Mg-Az, and sonicated in a Soniprep 150 sonicator (Curtin Matheson Scientific, Inc., Houston, Tex.) at 60% maximum setting for 3 pulses, 2 minutes each, in an ice-water bath. The sonicated preparation then was filtered through 0.22 μm Millex-GS filter (Millipore Corporation, Bedford, Me.), and dialyzed in 6,000–8,000 M.W. tubing. Molecular porous membrane tubing (Spectrum Medical Industries Inc., Los Angeles, Calif.) was used to dialyze the protein filtrate against 2 exchanges of distilled water and 2 exchanges of PBS-Mg-Az for about 4 hours each. Protein concentrations were measured by using the Bio-Rad Protein Assay kit (Bio-Rad Laboratories, Inc., Hercules, Calif.). This antigen preparation was immediately frozen in aliquots at –70° C. until used for coating plates.

To perform the ELISA, the antigen preparation was centrifuged at 500×g for 10 minutes, the supernatant was diluted to a final protein concentration of 10 pg/ml with coating buffer (0.05 M carbonate/bicarbonate buffer pH 9.6), and added at a volume of 100 μl/well to Immulon 1 flat bottom plates (Dynatech Laboratories, Inc., Chantilly, Va.). The antigen preparation was incubated in the plates at 4° C.

for 24 hours, and the plates were washed 3 times with NaCl-Tween-Azide plate washing solution. The serum samples were diluted (1:180 final dilution for mouse serum, 1:100 final dilution for human serum in these studies), and incubated with 50% FTA-ABS sorbent (Zeus Scientific Inc., Raritan, N.J.) for 1 hour to reduce nonspecific binding of bacterial antibodies, then added 50 µl/well to antigen-coated 96-well microplates and incubated for 1.5 hours at 37° C. After washing plates as above, 50 µl/well of a 1:4,000 dilution of anti-human or anti-mouse polyvalent immunoglobulin-alkaline phosphatase conjugate (Sigma, St. Louis, Mo.) was added to the plates and incubated for 2 hours. After additional washing plates as above, 50 µl/well of para-nitrophenyl phosphate alkaline phosphatase substrate (Sigma, St. Louis, Mo.) 2 mg/ml in substrate buffer was then added to the plates, and incubated 30 minutes for color development. The reaction was stopped by adding 50 µl/well of 5 N NaOH. The optical density (OD) at 405 nm ($A_{405}$) was measured by the EIA microplate reader (SLT-Labinstruments, Austria). The OD ratios (ODR) were calculated as: ODR=$(mOD_{sap}-mOD_b)/(mOD_{std}-mOD_b)$, where $mOD_{sap}$ is the average OD value of the duplicate OD readings of an experimental serum sample, $mOD_b$ is the average OD value of the duplicated OD readings of the blank, and $mOD_{std}$ is the average OD value of the duplicate OD readings of a pooled positive standard (pooled mouse serum from infected mice, or pooled human serum from Lyme patients).

D. Statistical Analysis

Each ELISA was repeated 3 times for mouse serum specimens, 2 times for human serum specimens, blinded to the identity of clinical/vaccination status or previous reactivity. The results were expressed as the mean ODR for each determination for vaccine studies, and as the mean OD ($mOD_{sample}-mOD_{blank}$) for ELISA sensitivity and specificity. The student's T test, assuming unequal variance, was used in the statistical analysis by the Microsoft Excel (version 5.0) for the Macintosh. The P values were from two tailed test; a P value of less than 0.05 was considered to indicate a significant difference.

E. Results

Figure 4:
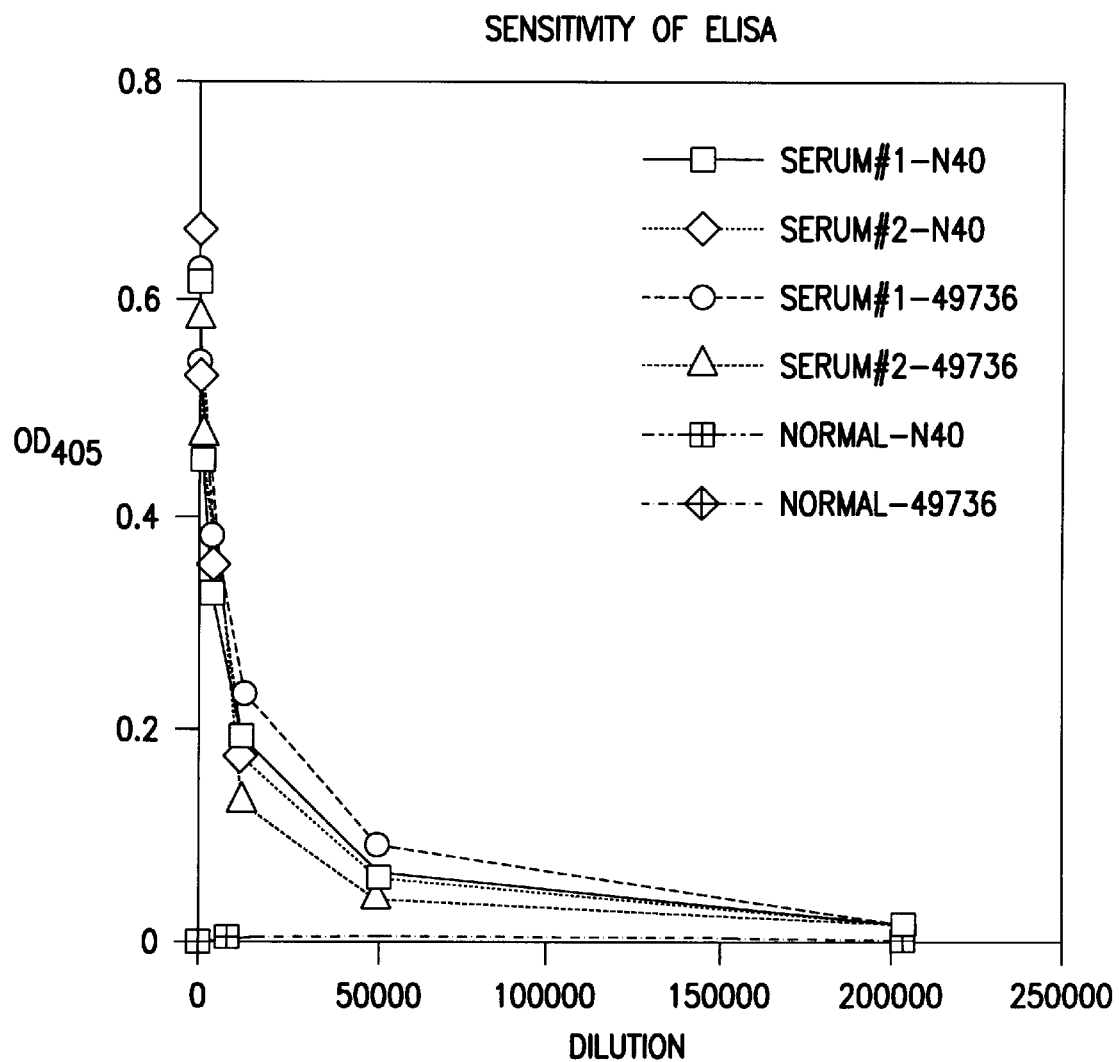
FIG. 4. Antibody titration curve comparing ELISAs prepared from *B. burgdorferi* isolates N40 and 49736.

The sensitivity of an OspA-minus ELISA for detection of B. burgdorferi antibody was evaluated by testing serially diluted strain N40 infected mouse sera with reference to an N40 antigen ELISA. The endpoint of antibody detection of 1:51,200 was obtained for both the N40 and 49736 antigen ELISAs, each of which contained identical concentrations (10 µg/ml) of B. burgdorferi antigen protein. FIG. 4 shows the antibody titration curve obtained for each of the two ELISAs (N40 and 49736) using two of the infected mouse sera (serum #1 and serum #2) and an uninfected control. The comparison of sensitivity of the two immunoassays was also determined by analyzing pooled Lyme positive and normal human specimens in duplicate. Mean OD values obtained from analysis of the positive serum pool in the N40 antigen ELISA ($OD_{N40}$) was 0.5475±0.0009 (mean±1 s.d.); the corresponding OD values obtained from the 49735 antigen ($OD_{49736}$) averaged 0.5355±0.00004. The mean OD for the negative pooled serum was 0.0131.

Positive $OD_{N40}$ and $OD_{49736}$ values were obtained from each of 20 individual sera from known Lyme seropositive human cases, and in 19 of 21 previous Lyme disease patients who were enrolled in a pilot vaccine safety trial. Negative results were obtained from 6 healthy blood donors. There were no significant OD differences between the N40 and 49736-based assays in any of these samples. These results suggest that the lack of OspA and OspB does not reduce the sensitivity of anti-B. burgdorferi antibody detection, and that 49736 antigen could be used to detect immunologic evidence of Lyme disease irrespective of the presence of anti-OspA reactivity.

EXAMPLE III

Discrimination of Vaccination, Infection and Vaccine Failure in Mice

To determine whether an ELISA based on strain 49736 can be used to distinguish between infection and vaccination under experimentally defined conditions, three groups of mice were studied: mice vaccinated with recombinant OspA or OspB fusion proteins, in which glutathione transferase (GT) was the fusion portion, and control mice vaccinated with a recombinant GT alone. Specifically, groups of female C3H/HeJ mice were immunized subcutaneously with 10 µg of recombinant OspA or OspB (both expressed as glutathione transferase (GT) fusion proteins) (E. Fikrig et al., Science, 250:553–6 (1990)) in complete Freunds adjuvant (Sigma Chemical Company, St. Louis, Mo.) and boosted at 14 days and 28 days with the same amount in incomplete Freunds adjuvant (Sigma Chemical Company, St. Louis, Mo.). Control mice were immunized with 10 µg of recombinant GT with the same regimen. Two weeks after the last booster vaccination, all mice were challenged with an intradermal inoculation of B. burgdorferi strain N40. The B. burgdorferi isolate N40 was grown as described in Example II. Mice were killed two weeks or four months after challenge inoculation. The blood was collected for the ELISA as described in Example II.

Figure 5:
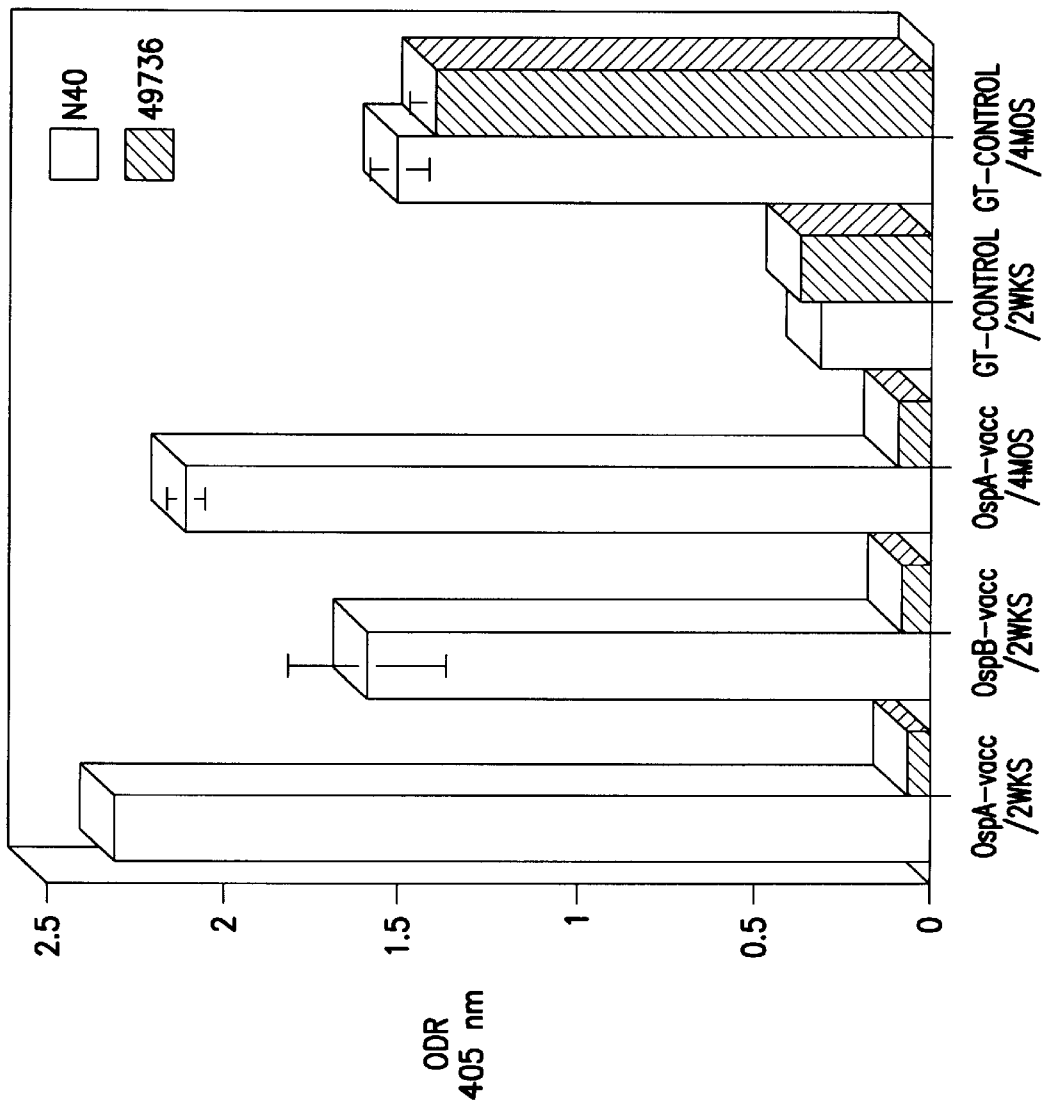
FIG. 5. Immunologic discrimination of vaccination, infection, and vaccine failure in mice.

FIG. 5 shows immunologic discrimination of vaccination, infection, and vaccine failure in mice. Each bar indicates the relative optical density ratio for the N40 and 49736 ELISAs for each group of sera tested. Specific groups of animals that were tested are indicated at the bottom of the chart. For five OspA- and five OspB-vaccinated mice, detectable antibody responses were observed when the N40 ELISA was used, regardless of whether the animals were protected against infection. The ODR of the conventional N40-based ELISA ($ODR_{N40}$) was 58.8 times higher than the ODR the 49736-based ELISA ($ODR_{49736}$) for the OspA protected animals (n=5, P<0.01). Among the OspB protected mice, the $ODR_{N40}$ was 31.0 times higher than $ODR_{49736}$ (n=4, P<0.01). Three OspA-protected animals were tested 4 months after inoculation; at this time point, the $ODR_{N40}$ was still 26.3 times higher than $ODR_{49736}$ (n=3, P<0.004). All of the GT-vaccinated control animals were N40 ELISA positive at 2 weeks (n=7), and 4 months (n=3) consistent with past studies demonstration the appearance of murine antibody responses between 7 and 14 days after infection. Thus, an N40-based ELISA could not distinguish between vaccination, infection, and vaccine failure in experimentally vaccinated and challenged mice.

Analysis of the same set of sera with the 49736 ELISA showed strikingly different results; background levels of ELISA reactivity were observed for sera tested from both groups of protected mice. Two vaccine failures were observed; one animal each in the OspA and OspB immunized groups were infected (as determined by culture of B. burgdorferi) at 4 months and two weeks post challenge, respectively. However, the $ODR_{49736}$ for the two vaccine failures was significantly higher than that achieved by the vaccine protected group (9.6 and 16.4 times, respectively), consistent with formation of antispirochete antibody responses (other than anti-OspA and OspB responses) during *B. burgdorferi* infection. Both mice had an anti-N40 antibody titers that were indistinguishable from the other vaccinated mice. Indeed, the antibody responses in the two vaccine failures were similar to those seen in the GT control animals; in the latter group ODR$_{N40}$ ELISA values were slightly higher at both time points than corresponding values from the 49736-based ELISA.

EXAMPLE IV

Analysis of Sera from Human Vaccine Trial Participants

To determine whether the immunoassay based on strain 49736 could be used to avoid serologic false positivity in vaccinated human subjects, paired human serum samples were obtained from participants in a recombinant OspA protein vaccine trial. Serum specimens from 20 individuals who were enrolled in the vaccine trial were kindly provided by the Block Island Medical Clinic (Block Island, R.I.). Fifteen enrollees received 3 or 30 µg doses of purified OspA as a vaccine antigen; five received a placebo. One of the vaccine recipients had evidence of previous exposure to *B. burgdorferi* by ELISA and Western blot. Blood samples were collected from individuals at day 0 and day 90 after they received the inoculation.

Figure 6:
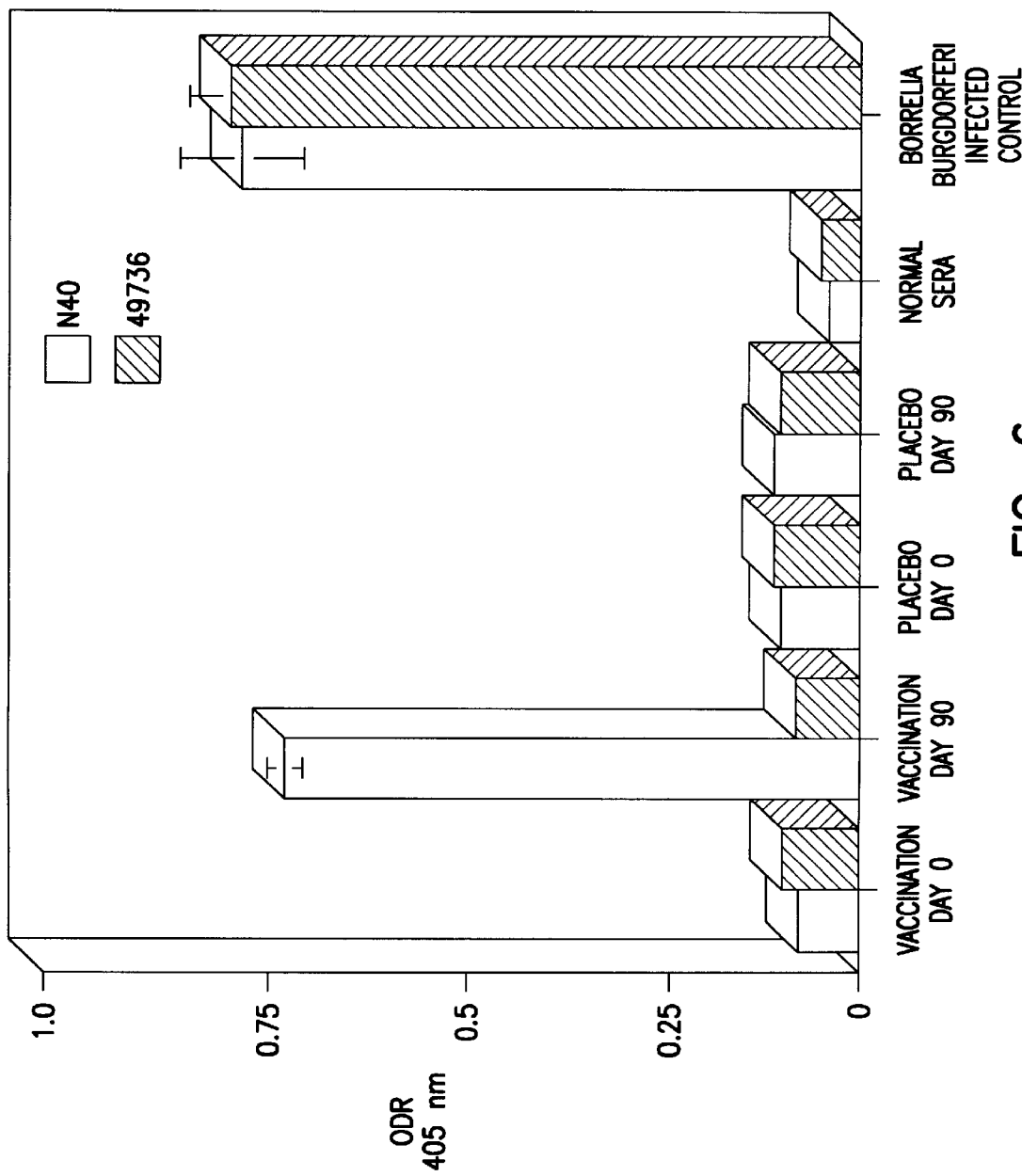
FIG. 6. Detection of characteristic vaccine response in humans vaccinated with recombinant OspA.

ELISAs using strain N40 and strain 49736 were performed as described in Example III. Results are shown in FIG. 6 and are expressed as mean optical density ratios (mODR) for the N40 and 49736-based ELISAs. Specimen types are indicated at the bottom of the chart. The cutoff value for a positive result was considered to be 5 times the mean ODR obtained from normal healthy blood donors (n=6); thus, the ODR cutoff for the N40 ELISA was 0.144, and for the 49736 ELISA was 0.149. As expected, for vaccine recipients at day 0, both mODR$_{N40}$ and mODR$_{49736}$ were below the cutoff; however, at day 90, while the mODR$_{49736}$ remained essentially unchanged, the mODR$_{N40}$ was positive at a mean 12.7 fold higher than the mODR$_{49736}$ (n=14, P<0.01) and 26.1-fold higher than normal pool. For participants vaccinated with the placebo, both mODR$_{N40}$ and mODR$_{49736}$ were below the cutoff at day 0 and day 90, and no significant differences between mODR$_{N40}$ and mODR$_{49736}$ were observed. Likewise, among seroreactive Lyme disease patients, mODR$_{N40}$ and mODR$_{49736}$ were both elevated an average of 27 times significantly higher than corresponding values from normals. Interestingly, one of the vaccine trial enrollees had a weak positive titer for both assays prior to vaccination; based on the absence of a discrepancy between the two immunoassays (ratio mODR$_{N40}$/mODR$_{49736}$=0.8) at day 0 and a slight increase in the mODR$_{N40}$ at day 90 (ratio 2.4), it appears likely that this enrollee may have had previous *B. burgdorferi* infection and experience a booster effect with the vaccine.

All cited papers and other publications are incorporated by reference herein, as though fully set forth. The invention has been described with reference to various specific and preferred embodiment and techniques. However, it should be understood that many variations and modifications may be made while remaining within the scope of the invention.

What is claimed is:

1. A method for detecting *B. burgdorferi* infection comprising:

(a) contacting a solid substrate comprising an immobilized amount of an antigen preparation of a purified whole cell lysate of an OspA⁻ *Borrelia burgdoferi* isolate, wherein said antigen preparation lacks a detectable level of outer surface protein A (OspA), with a sample of physiological fluid suspected of containing antibodies to *B. burgdorferi* for a period of time sufficient to allow formation of a binary complex between the immobilized antigen preparation and at least a portion of the antibodies, and wherein the subject has been vaccinated with a vaccine comprising all or a portion of OspA; and (b) detecting the presence of the binary complex on the solid substrate, wherein the presence of the binary complex is indicative of *B. burgdorferi* infection.

2. The method of claim 1 further comprising determining the amount of the binary complex on the solid substrate.

3. The method of claim 1 wherein the physiological fluid is blood, blood serum, blood plasma or cerebrospinal fluid.

4. The method of claim 3 wherein the physiological fluid is blood serum.

5. The method of claim 1 wherein the physiological fluid is obtained from a human subject.

6. The method of claim 5 wherein the vaccine further comprises all or a portion of outer surface protein B (OspB).

7. The method of claim 5 wherein step (b) comprises contacting the binary complex with anti-human immunoglobulin comprising a detectable label or a binding site for a detectable label, for a period of time sufficient to form a detectable ternary complex comprising the binary complex.

8. The method of claim 7 further comprising determining the amount of the ternary complex.

9. The method of claim 1 wherein the antigen preparation further lacks a detectable level of outer surface protein B (OspB) and wherein said vaccine comprises OspB.

10. The method of claim 1 wherein the *B. burgdorferi* isolate lacks a plasmid comprising a gene encoding OspA.

11. The method of claim 1, wherein the *Borrelia burgdorferi* isolate is 49736, 46047, 48510, 46794, 48081 or 50772.

* * * * *

UNITED STATES PATENT AND TRADEMARK OFFICE
CERTIFICATE OF CORRECTION

PATENT NO. : 6,045,804
DATED : April 4, 2000
INVENTOR(S) : Persing

It is certified that error appears in the above-identified patent and that said Letters Patent is hereby corrected as shown below:

Column 14,
Line 50, delete "48081".

Signed and Sealed this

Twenty-eighth Day of August, 2001

Attest:

*Nicholas P. Godici*

NICHOLAS P. GODICI
*Acting Director of the United States Patent and Trademark Office*

*Attesting Officer*